United States Patent [19]

McGarry

[11] Patent Number: 6,028,225
[45] Date of Patent: Feb. 22, 2000

[54] METHOD OF MAKING HYDROXY-SUBSTITUTED HYDROXYLAMINES AND COLOR DEVELOPERS CONTAINING SAME

[75] Inventor: Lynda W. McGarry, Spencerport, N.Y.

[73] Assignee: Eastman Kodak Company, Rochester, N.Y.

[21] Appl. No.: 09/153,681

[22] Filed: Sep. 15, 1998

[51] Int. Cl.⁷ .................................................. C07C 213/00
[52] U.S. Cl. ........................ 564/360; 564/409; 564/413; 564/453; 564/454; 564/487
[58] Field of Search ................................ 564/360, 409, 564/413, 487, 453, 454

[56] References Cited

U.S. PATENT DOCUMENTS 4,892,804  1/1990  Vincent et al. .
5,354,646  10/1994  Kobayashi et al. .
5,508,155  4/1996  Marrese et al. .

Primary Examiner—Samuel Barts
Attorney, Agent, or Firm—J. Lanny Tucker

[57] ABSTRACT

Hydroxy-substituted hydroxylamine antioxidants can be prepared by reacting hydroxylamine or a mono-substituted hydroxylamine, in free base form, with an epoxide. The antioxidant reaction product can be used without isolation from the reaction solution, and combined with a color developing agent to provide a photographic color developing composition in either concentrated or working strength formulations. The method for preparing the antioxidant is rapid and efficient because of the use of the free base form of the hydroxylamine reactant, higher temperatures (at or above 50° C.) and certain molar ratios of reactants.

9 Claims, 4 Drawing Sheets

METHOD OF MAKING HYDROXY-SUBSTITUTED HYDROXYLAMINES AND COLOR DEVELOPERS CONTAINING SAME

FIELD OF THE INVENTION

The present invention relates to a method of making hydroxylamine derivatives that can be used as antioxidants in color photographic developing compositions. This invention also relates to color developing compositions containing the antioxidants.

BACKGROUND OF THE INVENTION

Color developing solutions are used to process color photographic materials such as color photographic films and papers to provide the desired color images. Such solutions generally contain color developing agents, for example 4-amino-3-methyl-N-(β-methanesulfonamidoethyl)aniline, as reducing agents to react with color forming couplers in the photographic materials to form the desired dyes. However, such color developing agents are susceptible to oxidation by dissolved oxygen. An antioxidant is conventionally included in the color developing solutions to preserve the oxidation state of the color developing agent and thereby maintain useful color developing activity.

Many classes of compounds have been employed as color developing antioxidants, including hydroxylamines, hydroxamic acids, oximes, nitroxy radicals, hydrazines, hydrazides, phenols, saccharides, various simple amines, polyamines, quaternary ammonium salts, α-hydroxy ketones, alcohols, diamides and disulfonamides. To be used in practice, however, antioxidants must be soluble in aqueous media, non-toxic to living organisms, low cost and non-silver halide developers. Further, it is desirable that antioxidants react slowly with oxygen and rapidly with oxidized color developing agent, but not so rapidly that color development is retarded. Yet another concern is that the antioxidant must not promote bacterial growth. Preferably, such compounds are also odorless.

All of these considerations greatly limit the number and classes of compounds that practically can be used as antioxidants or stabilizers in color developing compositions. The compounds most often used in this fashion are hydroxylamine and mono- and dialkylhydroxylamine derivatives. They exhibit excellent characteristics by having a slow rate of aerial oxidation being non-silver halide developers, and are relatively inexpensive to produce. There are many publications describing such compounds including U.S. Pat. No. 4,892,804 (Vincent et al) and U.S. Pat. No. 5,354,646 (Kobayashi et al).

Unfortunately, many hydroxylamine derivatives have significant vapor pressure at room temperatures, and thus have a characteristic unpleasant odor. Considerable work has been carried out to improve various features of these compounds, including their water-solubility so odors are minimized. For example, various solubilizing groups, including hydroxyl, carboxyl and sulfonyl groups have been included in such compounds through simple reactions to reduce the odor problem.

Known procedures for preparing hydroxylamine derivatives having solubilizing groups, including hydroxyl groups, typically include one or more synthetic reaction steps and isolation of the product that is then added to color developing solutions. However, a simplified method to provide odorless color developer antioxidants is described in U.S. Pat. No. 5,508,155 (Marrese et al) and its counterpart patents. This method involves the reaction of a salt of hydroxylamine or a mono-substituted hydroxylamine derivative with a particular epoxide at room temperature for at least 8 hours (preferably up to 24 hours). The resulting product can be used in a color developing composition without isolation.

While this preparatory method represents an important advance in the art, it produces a number of by-products along with the desired product. In addition it requires too much reaction time for cost-effective scale up. Thus, there is a need in the industry for a means of producing hydroxy-substituted hydroxylamine derivatives in a more cost-effective manner with reduced by-products.

SUMMARY OF THE INVENTION

The problems noted above have been overcome with a method for preparing an antioxidant having structure I:

wherein R' is hydrogen, an alkyl group, a haloalkyl group, a hydroxyalkyl group, a cycloalkyl group, or an aryl group, $X_1$ is —C(OH)$R_2$CHR$_1$—, $X_2$ is —CHR$_1$C(OH)$R_2$—, $R_1$ and $R_2$ are independently hydrogen, an alkyl group, or a hydroxyalkyl group, or $R_1$ and $R_2$ together represent the carbon atoms necessary to complete a 5- to 8-membered carbocyclic ring, Y is an alkylene group having at least 4 carbon atoms and an even number of carbon atoms in the chain, or Y is an aliphatic group having at least 4 carbon or oxygen atoms in the chain and an even number of atoms in the chain, and m, n and p are independently 0 or 1, the method comprising adding an epoxide having either structure II or III:

wherein R', $R_1$, $R_2$ and Y are as defined above, to an aqueous solution of hydroxylamine or a mono-substituted hydroxylamine, in free base form, at such a rate as to maintain the reaction temperature of the reaction solution of at least 50° C., and the molar ratio of the total amount of epoxide added to the hydroxylamine or mono-substituted hydroxylamine being from about 2:1 to about 2:1.2.

This invention also provides the aqueous reaction solution resulting from the noted production method, and a working strength color developing composition comprising a photographic color developing agent, and a reaction solution of a hydroxylamine antioxidant obtained as described above.

This invention further provides a method for preparing a photographic color developing composition comprising:

A) preparing the substituted hydroxylamine antioxidant in a reaction solution as described above, and B) without separation of the hydroxylamine antioxidant from the reaction solution, mixing the hydroxylamine antioxidant with a photographic color developing agent.

Further, a method for photographic processing comprises treating an imagewise exposed, color photographic silver halide element with the color developing composition described above.

The present invention provides a highly useful color developing composition that is stable to aerial oxidation because of the presence of a suitable hydroxy-substituted hydroxylamine as the antioxidant. Moreover, this antioxidant is highly water-soluble, thereby reducing the objectionable odor that might otherwise be present. The solubilizing groups are added to the hydroxylamine starting material in a rapid and simple synthetic procedure using an epoxide as a co-reactant. The resulting reaction solution contains fewer by-products, and can be mixed with a color developing agent without the need to isolate the antioxidant from its reaction solution. Because of fewer by-products, the reaction solution can more readily be assayed for product using titrimetric and chromatographic methods.

The advantages outlined above are achieved by using the free base form of the hydroxylamine (or its mono-substituted derivative) in the reaction rather than the more common hydroxylamine salt (such as a hydroxylamine sulfate). In addition, the epoxide is added to an aqueous reaction solution at a rate sufficient to maintain a higher reaction temperature due to the exotherm from the reaction. The total amount of reactants is controlled to achieve highest stability and reduced by-products so that the molar ratio of epoxide to hydroxylamine reactant is from about 2:1 to about 2:1.2.

DETAILED DESCRIPTION OF THE INVENTION

As noted above, the color developing compositions of this invention are prepared by mixing a photographic color developing agent with a hydroxy-substituted hydroxylamine antioxidant prepared as described below. Generally, the antioxidant is prepared from the reactants in a reaction solution and used in that reaction solution without separation therefrom. In this manner, the antioxidant has been prepared in situ, and not separated in any manner from the reaction solution before its use. It is not necessary, however, that the reaction solution containing the reactants be used immediately. Rather, it can be stored for later use, or mixed with the color developing agent and then stored for later use. By "separation" is meant any physical or chemical means for taking the hydroxy-substituted hydroxylamine reaction product from the reaction solution prior to use with the color developing agent. This costly and time consuming separation step(s) is avoided with the practice of this invention.

The color developing composition resulting from mixing the antioxidant reaction solution with a color developing agent (and any other useful components) can be used as a working strength photoprocessing bath or replenisher, or it can be formulated in a concentrated form.

Mono-substituted hydroxylamines useful as one reactant in the practice of the present invention can be generally defined as "hydroxylamines" having one monovalent aliphatic or aromatic substituent connected to the nitrogen atom. Such substituents are well understood in the art as including monovalent acyclic or cyclic hydrocarbon groups, aromatic carbocyclic groups, and monovalent heterocyclic groups. Monosubstituted hydroxylamines are described, for example, in U.S. Pat. No. 5,091,292 (Fujimoto et al), U.S. Pat. No. 5,094,937 (Morimoto et al), and U.S. Pat. No. 5,100,765 (Fujimoto).

More specifically, the useful hydroxylamines can be defined as R"N(OH)H wherein R" is hydrogen, a substituted or unsubstituted alkyl group of 1 to 10 carbon atoms (such as methyl, ethyl, propyl, isopropyl, hydroxymethyl, 2-hydroxyethyl, pentyl, t-butyl, benzyl and octyl), a substituted or unsubstituted cycloalkyl group of 5 to 10 carbon atoms (such as cyclopentyl, cyclohexyl, 4-methylcyclohexyl and cyclooctyl) or a substituted or unsubstituted aryl group of 6 to 10 carbon atoms (such as phenyl, naphthyl, xylyl, 4-hydroxyphenyl and tolyl). Other substituted alkyl, cycloalkyl and aryl groups would be readily apparent to one skilled in the art. Preferably R" is hydrogen or alkyl groups of 1 to 4 carbon atoms. Most preferably, R" is hydrogen.

Particularly useful mono-substituted hydroxylamines include, but are not limited to, N-methylhydroxylamine, N-isopropylhydroxylamine, and N-ethylhydroxylamine.

It is essential that hydroxylamine or the mono-substituted derivatives used in the invention be in the free base form, meaning that they are not present as acid salts, such as sulfates or hydrochlorides. Thus, no hydroxylamine salts are contemplated for use in this invention, and no chemical bases need to be added to the reaction mixture to neutralize the reactant salts.

The hydroxylamine or mono-substituted hydroxylamines described above are reacted under suitable conditions (described below) with a mono-, di-, tri- or tetra-substituted epoxide, that is, epoxides having one to four substituents on the two carbons in the epoxide ring. Such substituents include those described above in the definition of the hydroxylamines.

More specifically, however, these epoxides can be defined as having either structure (II) or (III):

II

III wherein R' is hydrogen, or an alkyl group of 1 to 10 carbon atoms (such as methyl, ethyl, isopropyl, t-butyl, pentyl, hexyl, benzyl, octyl, decyl and 3-methylhexyl). By "alkyl group" is meant any unsubstituted linear or branched alkyl group having the noted carbon atoms, as well as a linear or branched alkyl group substituted with one or more phenyl or hydroxyphenyl groups, as long as the maximum number of carbon atoms is not exceeded. Preferably, R' is a substituted or unsubstituted alkyl group of 1 to 7 carbon atoms, and more preferably, the alkyl group has 1 to 3 carbon atoms.

R' can also be a substituted or unsubstituted haloalkyl group of 1 to 10 carbon atoms (such as those alkyl groups described above with one or more hydrogen atoms replaced with one or more halo atoms). The haloalkyl group can have one or more halo substituents chosen from chloro and bromo. Preferably, the haloalkyl group has 1 to 3 carbon atoms and one or two chloro substituents, and more preferably, it has a single chloro group. In this category of R' groups, most preferably, it is chloromethyl or 2-chloroethyl.

R' can further be a substituted or unsubstituted hydroxyalkyl group of 1 to 10 carbon atoms (such as hydroxymethyl, 2-hydroxyethyl, 1-hydroxyethyl, 2-hydroxypropyl, 2,3-dihydroxypropyl, 1-hydroxyoctyl and 1,3-dihydroxydecyl). By "hydroxyalkyl group" is meant an alkyl group having the noted carbon atoms substituted with one or more hydroxy groups anywhere on the molecule that is technically possible, and optionally one or more other substituents as described above for the "alkyl group". Preferably, in this embodiment, R' is an unsubstituted hydroxyalkyl group of 1 to 3 carbon atoms having only one hydroxyl group, and more preferably, it is hydroxymethyl.

In the noted formulae II and III, R' can also be an aryl group having 6 to 10 carbon atoms in the ring structure (such as phenyl, xylyl, tolyl, naphthyl and 4-hydroxyphenyl). By "aryl group" is meant an unsubstituted phenyl or naphthyl group, or one of those groups having one or more alkyl (as defined above) or hydroxy groups at any position of the ring that does not interfere with the reactive properties or solubility of the epoxide. The aryl group can also include a phenyl ring having non-aromatic carbocyclic or heterocyclic ring structures fused thereto. Preferably, when R' is an aryl group, it is a substituted or unsubstituted phenyl group, and more preferably it is phenyl.

R' can also be a cycloalkyl group having 5 to 10 carbon atoms in the ring structure (such as cyclopentyl, cyclohexyl, 4-methylcyclohexyl and 3-hydroxycyclohexyl). By "cycloalkyl group" is meant any unsubstituted cycloalkyl having the requisite carbon atoms, as well as cycloalkyl rings substituted with one or more alkyl (as defined above) or hydroxyl groups. Preferably, as a cycloalkyl group, R' is cyclohexyl.

$R_1$ and $R_2$ are independently hydrogen, a substituted or unsubstituted alkyl group of 1 to 2 carbon atoms (that is a methyl or ethyl group that can be substituted as described above for "alkyl group"), or a substituted or unsubstituted hydroxyalkyl group of 1 to 2 carbon atoms (that is methyl or ethyl having one or more hydroxy substituents).

Alternatively, $R_1$ and $R_2$ together can represent the carbon atoms necessary to complete a 5- to 8-membered saturated or partially saturated carbocyclic ring structure (of one or more fused rings) which can be unsubstituted or substituted with one or more alkyl groups of 1 to 3 carbon atoms (as defined above) or one or more hydroxyalkyl groups of 1 to 3 carbon atoms (as defined above). By "partially saturated" is meant that the ring structure contains at least one double bond, but the ring structure is not aromatic.

In a preferred embodiment, Y is defined as an alkylene group having at least 4 carbon atoms and further having an even number of carbon atoms in the chain. By "alkylene group" is meant a branched or linear unsubstituted alkylene (such as methylene, dimethylene and trimethylene) as well as an alkylene group which has one or more substituents which are simple alkyl groups of 1 to 2 carbon atoms or hydroxy.

In another embodiment, Y is a divalent aliphatic group in which the sum of carbon and oxygen atoms in the chain is an even number, provided there are at least 4 atoms in the chain. Such groups can be substituted or unsubstituted oxyalkylene, alkyleneoxy, oxyalkylene, oxyalkyleneoxy, alkyleneoxyalkylene, and similar combinations of such groups that would be readily apparent to one skilled in the art.

Particularly useful epoxides in the practice of this invention include the following compounds: glycidol, ethylene oxide, propylene oxide, 2-methyl-2,3-epoxy-1-propanol, 4-phenyl-2,3-epoxy-1-butanol, 1,4-butanediol diglycidyl ether, epichlorohydrin and 1,2,7,8-diepoxyoctane. Glycidol is most preferred.

The hydroxylamine antioxidants useful in the practice of this invention are prepared using the following general procedure and conditions.

One or more hydroxylamines (in free base form) as defined above are provided in an aqueous solution. The concentration in the solution can vary, but is generally up to 17 mol/l, and more typically from about 1 to about 5 mol/l. One or more epoxides as defined above are then added to the solution for reaction. The rate of reaction is controlled so that the reaction is as rapid as possible, but slow enough to control the expected exotherm and to prevent refluxing. Generally, the addition rate of the epoxide(s) to the reaction solution is at least 0.1 mol %/min, and preferably from about 0.1 to about 4 mol %/min. The rate of addition can thus vary considerably depending upon the reaction rate of a particular set of reactants, the reaction temperature desired and the desired yield. The "mol %/min" rate is in reference to the total moles of epoxide to be used in the reaction. Epoxide addition can be continuous or intermittent depending on the particular equipment and reactants used, and the ability of the operator to control reaction temperature.

Reaction begins immediately upon addition of epoxide, and it may be allowed to continue beyond its addition. The time of reaction can vary depending upon many factors including the given set of reactants, reaction temperature, desired yield and mode of epoxide addition. Generally, the reaction carried out in as short as time as it practical under the set of circumstances. Preferably, it is finished within 8 hours (and more preferably within 4 hours). Suitable agitation may be used at any time during the reaction.

The reaction temperature can be carried out at any suitable temperature, but lower reaction temperatures tend make the reaction impractically slow. Thus, the reaction temperature is generally maintained at 50° C. or more, and preferably it is from about 70 to about 95° C. This higher reaction temperature allows for a more rapid reaction, and can be provided by the reaction exotherm or by using externally applied heat. Thus, the reaction can be begun at considerably lower temperature while allowing the exotherm to raise the temperature of the reaction mixture to the desired level. Alternatively, the reaction solution can be preheated to the desired reaction temperature before addition of the epoxide (s).

The reaction solution containing the antioxidant reaction product can be used to prepare color developing compositions without isolation, or it can be diluted or concentrated for storage and later use.

The reactants used in making the antioxidant can be obtained from a number of commercial sources, including but not limited to, Nissin Chemical Company, Dixie Chemical Company, Angus Chemicals, BASF, and Aldrich Chemical Company. Alternatively, it would not be difficult for a skilled worker to make the noted epoxides or mono-substituted hydroxylamines using known procedures and readily available starting materials.

The resulting hydroxylamine antioxidants can be defined by the structure (I)

wherein R', $R_1$, $R_2$, $X_1$, $X_2$ and Y are as defined above. In addition, p is 0 or 1 (preferably, p is 0), m and n are independently 0 or 1, and preferably each is 1.

Specific di-substituted hydroxylamine antioxidants prepared by and useful in this invention include, but are not limited to: N,N-bis(2,3-dihydroxypropyl)-hydroxylamine, N,N-bis(2-methyl-2,3-dihydroxypropyl)hydroxylamine and N,N-bis(1-hydroxymethyl-2-hydroxy-3-phenylpropyl) hydroxylamine. The first compound is preferred.

More than one antioxidant can be simultaneously prepared and included in the color developing compositions of this invention by reacting the appropriate multiple epoxides and mono-substituted hydroxylamines in the reaction solution. Preferably, however, only one antioxidant is prepared and used for each color developing composition.

The color developing compositions of the present invention include one or more color developing agents, of which there are hundreds of possibilities. Useful classes of such materials include, but are not limited to, aminophenols, p-phenylenediamines (especially N,N-dialkyl-p-phenylenediamines) and others which are well known in the art. Further details of such materials are provided in Research Disclosure, publication 38957, pages 592–639 (September, 1996), and references cited therein. Research Disclosure is a publication of Kenneth Mason Publications Ltd., Dudley House, 12 North Street, Emsworth, Hampshire PO10 7DQ England (also available from Emsworth Design Inc., 121 West 19th Street, New York, N.Y. 10011). This reference will be referred to hereinafter as "Research Disclosure".

Particularly useful color developing agents include, but are not limited to, N,N-diethyl p-phenylenediamine sulfate (KODAK Color Developing gent CD-2), 4-amino-3-methyl-N-(2-methane sulfonamidoethyl)aniline sulfate, 4-(N-ethyl-N-β-hydroxyethylamino)-2-methylaniline sulfate (KODAK Color Developing Agent CD-4), p-hydroxyethylethylaminoaniline sulfate, 4-(N-ethyl-N-2-methanesulfonylaminoethyl)-2-methylphenylenediamine sesquisulfate or 4-amino-3-methyl-N-ethyl-N-(β-methanesulfonamidoethyl)aniline (KODAK Color Developing Agent CD-3), 4-(N-ethyl-N-2-methanesulfonylaminoethyl)-2-methylphenylenediamine sesquisulfate, and others readily apparent to one skilled in the art. KODAK Color Developing Agent CD-3 is preferred in the practice of this invention.

The color developing composition can be easily prepared by mixing a suitable color developing agent (in a suitable solution) with a portion of the original reaction solution (diluted or concentrated) containing the antioxidant as described above. Water can be added to the resulting composition to provide the desired concentrations, and the pH can be adjusted to the desired value with a suitable chemical base (such as sodium hydroxide).

The amounts of hydroxylamine antioxidant and color developing agent generally and preferably present in the color developing compositions of this invention are listed in the following table. These ranges are considered approximate (thus each range end point is considered to be "about"). Generally, the molar ratio of antioxidant to color developing agent can vary widely but is usually from about 0.1:1 to about 4:1.

| COMPONENT | GENERAL AMOUNT (mol/l) | PREFERRED AMOUNT (mol/l) |
|---|---|---|
| Hydroxylamine antioxidant | 0.0001–1 | 0.005–0.5 |
| Color developing agent | 0.0001–1 | 0.01–1 |

The color developing composition of this invention can further include one or more of a variety of other addenda which are commonly used in such compositions, such as alkali metal halides (such as potassium chloride, otassium bromide, sodium bromide and sodium iodide), metal sequestering gents (such as aminopolycarboxylic acids), buffers to maintain pH from about 9 to about 13 (preferably from about 9 to about 11), such as carbonates, phosphates and borates, sulfites, development accelerators, fragrances, optical brightening agents, wetting agents, surfactants and water-soluble or water-dispersible couplers as would be understood by one skilled in the art (see for example, Research Disclosure, noted above). The amounts of such additives are well known in the art also.

Another useful component of the color developing composition, especially when formulated in concentrated form, is a photographically inactive, water-miscible or water-soluble, straight-chain organic solvent that is capable of dissolving color developing agents in their free base forms. Such organic solvents can be used singly or in combination, and preferably each has a molecular weight of at least 50, and preferably at least 100, and generally 200 or less and preferably 150 or less. Such preferred solvents generally have from 2 to 10 carbon atoms (preferably from 2 to 6 carbon atoms, and more preferably from 4 to 6 carbon atoms), and can additionally contain at least two nitrogen or oxygen atoms, or at least one of each heteroatom. The organic solvents are substituted with at least one hydroxy functional group, and preferably at least two of such groups. They are straight-chain molecules, not cyclic molecules.

By "photographically inactive" is meant that the organic solvents provide no substantial positive or negative effect upon the color developing function of the concentrate.

Useful organic solvents include, but are not limited to, polyols including glycols (such as ethylene glycol, diethylene glycol and triethylene glycol), polyhydroxyamines (including polyalcoholamines), and alcohols (such as ethanol and benzyl alcohol). Glycols are preferred with ethylene glycol, diethylene glycol and triethylene glycol being most preferred. Of the alcohols, ethanol and benzyl alcohol are most preferred. The most preferred organic solvent is diethylene glycol. Further details of the use of such organic solvents, and useful amounts are provided in copending and commonly assigned U.S. Ser. No. 09/132,200 filed Aug. 11, 1998 by Darmon et al and entitled "Homogeneous Single-Part Photographic Color Developing Concentrate and Method of Making".

The color developing composition of this invention can be formulated as working strength solutions in processing tanks, replenishers, or concentrates, for any suitable photoprocessing use.

The color developing composition of this invention has obvious utility to provide color development in an imagewise exposed color photographic silver halide element comprising a support and one or more silver halide emulsion layers containing an imagewise distribution of developable silver halide emulsion grains. A wide variety of types of photographic elements (both color films, color papers and color motion picture films and prints) containing various types of emulsions can be processed using the present invention, the types of elements being well known in the art (see *Research Disclosure*, noted above). In particular, the invention can be used to process color photographic silver halide papers or other "display" elements, particularly color papers having high silver chloride (greater than 90 mol % chloride based on total silver) photosensitive emulsions. The color developing compositions can also be used in processing of color reversal films and papers.

Color development is generally carried out by contacting the element under suitable time and temperature conditions, in suitable processing equipment, to produce the desired color image. Additional processing steps can then be carried out using conventional procedures, including but not limited to, steps to desilver the element (bleaching and fixing or bleach/fixing), washing (or rinsing), stabilizing and drying, in any particular desired order. Useful processing steps, conditions, and materials are well known (see for example, *Research Disclosure* noted above).

The following examples are provided to illustrate the practice of the invention and not to limit it in any way. Unless otherwise indicated, percentages are by weight.

EXAMPLE 1
Laboratory Scale Preparation of Hydroxylamine Antioxidant

This example demonstrates a typical procedure for preparing antioxidants according to the present invention.

A two-liter, three necked flask equipped with a mechanical stirrer and blade, a reflux condenser, thermometer, nitrogen inlet and an addition funnel was charged with a 50% aqueous hydroxylamine solution (209.4 ml, 234.53 g, 3.547 moles), and diluted with 547 ml of deionized water. The solution was warmed to 60° C. using an oil bath. The reaction was monitored using an FTIR probe by circulating the solution through an IR cell and taking spectra every three minutes. The concentration of each species was calculated after each sampling from a distinct peak for each species and was graphed with time (see FIG. 4).

Glycidol (96%, 490 ml, 547.33 g, 7.094 moles) was added to the solution at a rate of about 2.1 ml/min. The temperature of the resulting reaction mixture began to rise, and the mixture began to reflux. Epoxide addition was completed within 1.5 hours, and the reaction was allowed to proceed for another 30 minutes. After cooling, the reaction mixture volume was 1143 ml having a mass of 1293.1 g.

The theoretical yield of the desired product N,N-bis-(2,3-dihydroxypropyl)hydroxylamine is 49.37% (3.1 moles), and the actual calculated yield was 49.1% as determined by titrimetric and chromatographic methods. Thus, the overall yield was about 99%. Aqueous solutions of the noted compound did not have any objectionable odor.

Similar reaction methods were carried out at different reaction temperatures, and the course of each reaction was followed using an FTIR probe placed in the flask to monitor the disappearance of reactants and the appearance of the desired product. All of the reactions were carried out using the same ratios of reactants as described above in this example. In all of FIGS. 1–4, the curves identified with "X" show the change in hydroxylamine reactant concentration. Similarly, the curves identified with "Y" show the change in glycidol reactant concentration, and the curves identified with "Z" show the change in substituted hydroxylamine product concentration.

Figure 1:
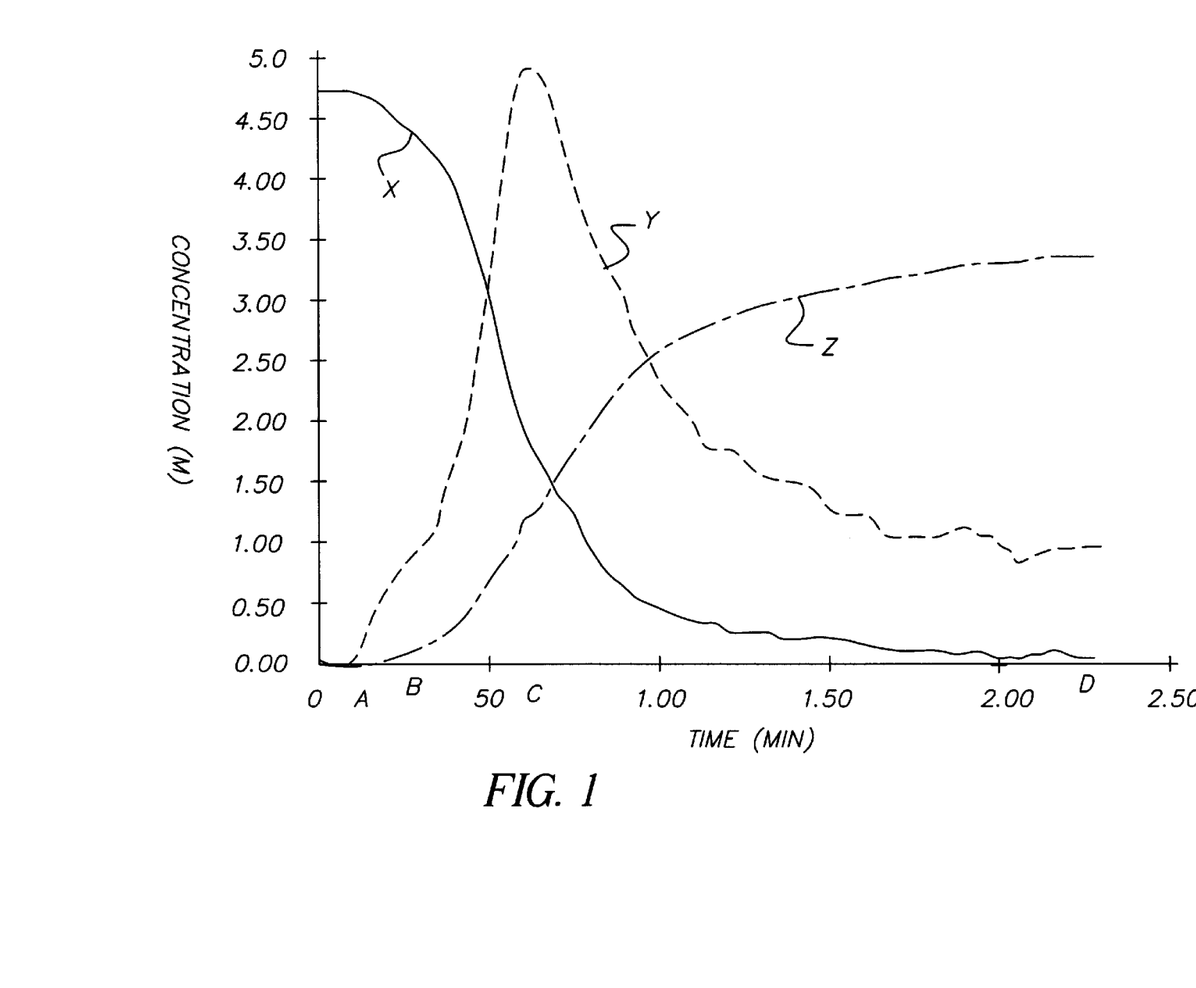
FIG. 1 is a graphical representation of a reaction carried out at 0–22° C. as described in Example 1 below.

The results of a reaction carried out wherein the reaction temperature is maintained at 0–22° C. is shown in FIG. 1. On the time scale, at point "A" (10 minutes) glycidol addition was begun and the reaction temperature was 10° C. At point "B" (25 minutes), the reaction temperature had increased to 12° C. and the glycidol addition rate was increased. At point "C" (60 minutes), glycidol addition was complete and the reaction temperature was 19° C. Point "D" represents 225 minutes of reaction time at which point the reaction temperature was 22° C. It can be seen that glycidol built up to a significant concentration in the reaction mixture before the reaction began at a significant rate. This long induction period might not be acceptable under certain circumstances (such as large-scale production methods) since side reactions could occur resulting in undesirable by-products as the glycidol concentration increases.

Figure 2:
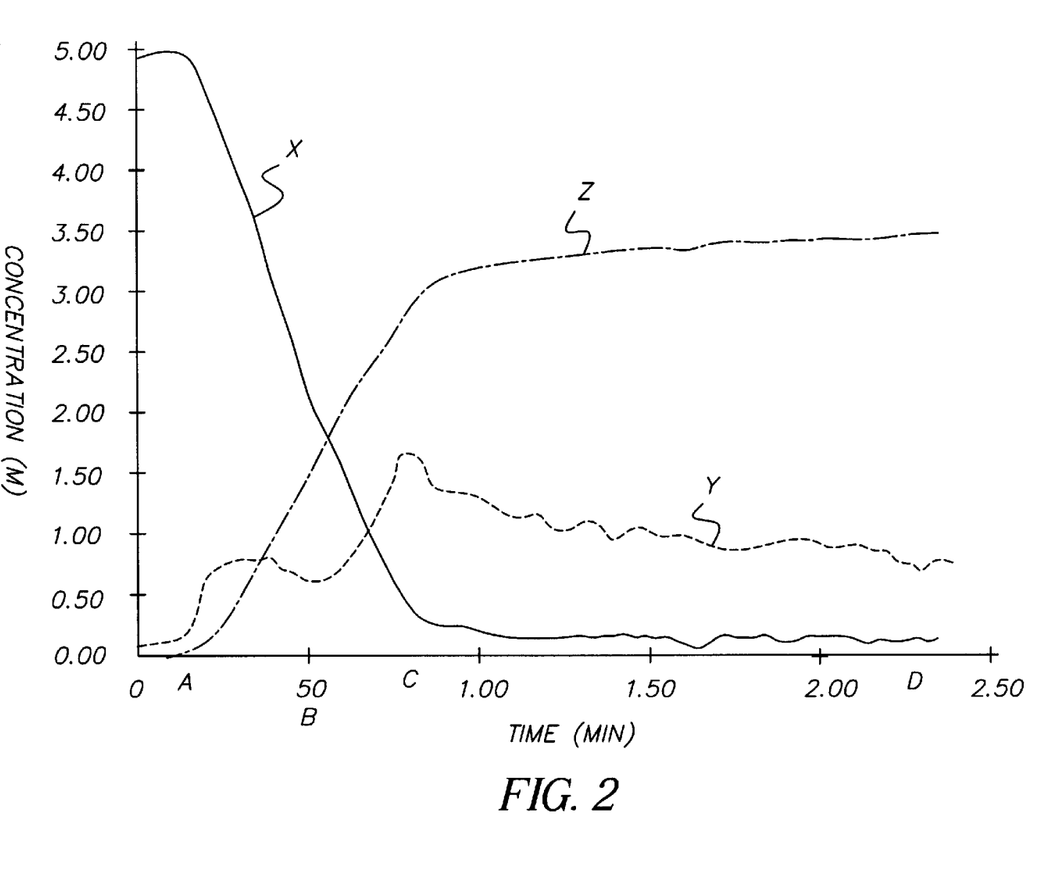
FIG. 2 is a graphical representation of a reaction carried out at 25–48° C. as described in Example 1 below.

In FIG. 2, the results can be seen for a reaction begun at 25° C., but in which the reaction temperature was allowed to increase and was maintained at about 48° C. The reaction began much faster than when the reaction temperature was 0–22° C. (FIG. 1). In FIG. 2, point "A" (10 minutes) represents the point at which glycidol addition was begun at the reaction temperature was 25° C. At point "B" (50 minutes), the reaction temperature had increased to 48° C. At point "C" (80 minutes), glycidol addition was complete and the temperature was maintained at 48° C. The reaction was completed at point "D" (225 minutes) and the reaction temperature had dropped to 25° C.

Figure 3:
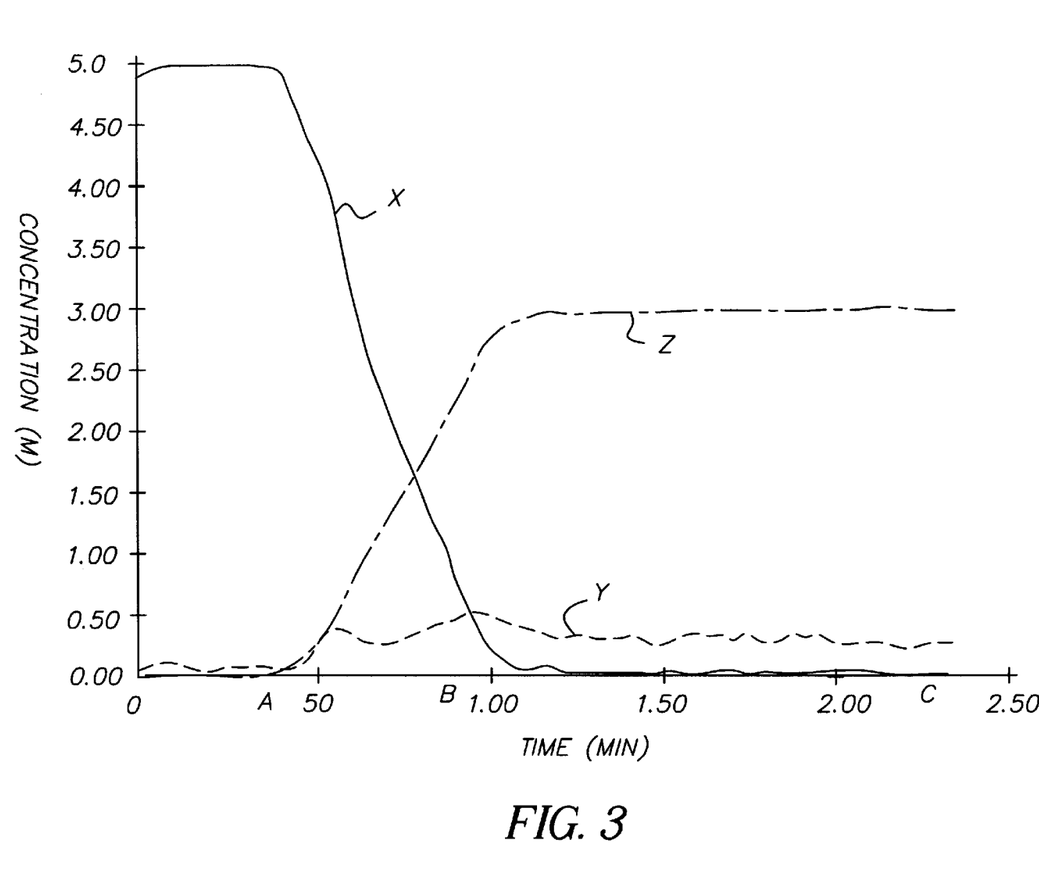
FIG. 3 is a graphical representation of a reaction carried out at 50–62° C. as described in Example 1 below.

The effect of temperature is even more evident in FIG. 3 that shows the results for a reaction mixture that was preheated to 50° C. before glycidol addition. The hydroxylamine reactant remained stable at that temperature, and reacted steadily upon addition of epoxide as it was added. The glycidol concentration was maintained at low levels throughout the reaction, thus giving undesirable by-products little time to form. Point "A" (40 minutes) was the time glycidol addition was begun. At point "B" (95 minutes), glycidol addition was complete and the reaction temperature had risen to 62° C. At point "C" (220 minutes), the reaction was complete and the reaction temperature had dropped to 50° C.

Figure 4:
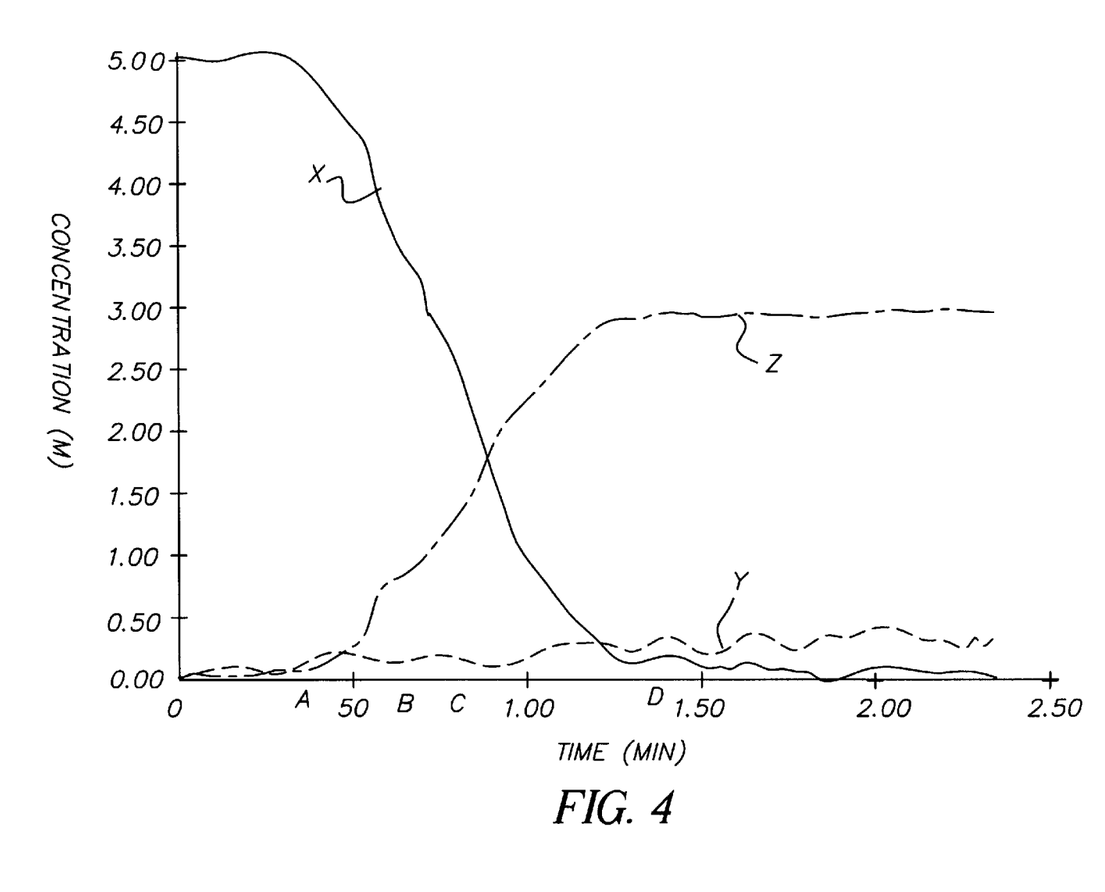
FIG. 4 is a graphical representation of a reaction carried out at 60–100° C. as described in Example 1 below.

FIG. 4 shows the results from Example 1 in which the reaction mixture was preheated to 60° C., followed by glycidol addition that was rapid enough to bring the reaction mixture to reflux. Thus, reaction was essentially instantaneous with no further reaction product formed after glycidol addition was completed. It may not be desirable in every instance to bring the reaction mixture to reflux, but the reaction temperature can be readily monitored to maintain an optimum reaction temperature for this set of reactants of from about 60 to about 90° C. At point "A" (40 minutes), glycidol addition was begun. At point "B" (60 minutes), the reaction temperature had increased to 80° C. and the glycidol rate of addition was increased. At point "C" (80 minutes), the reaction temperature had increased to 100° C., and at point "D" (140 minutes), glycidol addition was complete and the reaction temperature remained at 100° C.

EXAMPLE 2
Large Scale Preparation of Hydroxylamine Antioxidant

A twelve-liter, three necked flask equipped with a mechanical stirrer and blade, a reflux condenser, thermometer, nitrogen inlet and an addition funnel was charged with a 50% aqueous hydroxylamine solution (1675 ml, 1.875 kg, 28.375 moles), and diluted with 4375 ml of deionized water.

Glycidol (96%, 3919 ml, 4377.5 g, 56.75 moles) was added to the aqueous solution at room temperature. As the addition continued, the temperature of the resulting reaction mixture began to rise, and epoxide addition was continued at a rate sufficient to keep the temperature between 80 and 95° C. Epoxide addition was completed within 3 hours, and the reaction was allowed to cool to room temperature. The reaction mixture volume was 9.2 liters having a mass of 10.516 kg.

The theoretical yield of the desired product N,N-bis-(2,3-dihydroxypropyl)hydroxylamine is 48.56% (3.08 moles), and the actual calculated yield was 48.5% as determined by titrimetric and chromatographic methods (essentially 100% yield). Aqueous solutions of the noted compound did not have any objectionable odor.

EXAMPLE 3
Alternative Preparation of Color Developing Composition

Example 1 was repeated except that propylene oxide was used in place of glycidol at the same molar amount relative to the hydroxylamine reactant. Analysis showed that the desired substituted hydroxylamine product was obtained.

EXAMPLE 4
Preparation of Color Developing Composition

This example demonstrates the preparation of a useful photographic color developing composition according to the present invention. The components of the composition as shown in TABLE I below, were provided as three parts, and then mixed together to form working strength, replenisher and concentrated color developing compositions of this invention.

TABLE I

| PART | COMPONENT | WORKING STRENGTH (per liter) | REPLENISHER (per liter) | CONCENTRATE (per liter) |
|---|---|---|---|---|
| A | Lithium salt of sulfonated polystyrene (30% w/w) | 0.172 g | 0.182 g | 3.700 g |
|  | Triethanolamine (85%) | 7.301 g | 7.301 g | 157.000 g |
|  | KODAK EKTAPRINT ™ 2 Stain Reducing Agent | 0.674 g | 1.174 g | 25.24 g |
|  | N,N-bis(2,3-dihydroxypropyl)hydroxylamine (50%, 3.1 mol/l)* | 5.224 g | 6.205 g | 133.433 g |
| B | Lithium sulfate (anhydrous) | 2.000 g | 2.000 g | 84.39 g |
|  | Potassium sulfite (45%) | 0.835 g | 0.835 g | 35.23 g |
|  | 4-Amino-3-methyl-N-ethyl-N-(β-methanesulfon-amidoethyl)aniline | 4.65 g | 6.783 g | 286.2 g |
| C | 1-Hydroxyethylidene-1-diphosphonic acid (60% w/w) | 0.86 g | 0.86 g | 12.89 g |
|  | Potassium chloride | 5.733 g | 4.000 g | 59.97 g |
|  | Potassium bromide | 0.028 g | 0.025 g | 0.375 g |
|  | Potassium hydroxide (45.5%) | 4.58 g | 4.576 g | 68.6 g |
|  | Potassium carbonate (47%) Water to 1 liter solution pH adjusted to 10–11 with sodium hydroxide | 52.63 g | 52.63 g | 789.1 g |

*Solution of Example 1.

EXAMPLE 5
Processing Photographic Element

The color developing composition of Example 3 was used to process samples of a color photographic silver halide color paper, namely KODAK EDGE 7 Color Paper, which had been imagewise exposed. After bleach/fixing using the commercially available EKTACOLOR Bleach/Fix processing solution and washing, suitable color images were obtained.

The invention has been described in detail with particular reference to preferred embodiments thereof, but it will be understood that variations and modifications can be effected within the spirit and scope of the invention.

I claim:

1. A method for preparing an antioxidant having the structure I:

wherein R' is hydrogen, an alkyl group, a haloalkyl group, a hydroxyalkyl group, a cycloalkyl group, or an aryl group, $X_1$ is —C(OH)$R_2$CH$R_1$—, $X_2$ is —CH$R_1$C(OH)$R_2$—, $R_1$ and $R_2$ are independently hydrogen, an alkyl group, or a hydroxyalkyl group, or $R_1$ and $R_2$ together represent the carbon atoms necessary to complete a 5- to 8-membered carbocyclic ring, Y is an alkylene group having at least 4 carbon atoms and an even number of carbon atoms in the chain, or Y is an aliphatic group having at least 4 carbon or oxygen atoms in the chain and an even number of atoms in the chain, and m, n and p are independently 0 or 1, said method comprising adding an epoxide having either structure II or III:

-continued

III wherein R', $R_1$, $R_2$ and Y are as defined above,
to an aqueous solution of hydroxylamine or a monosubstituted hydroxylamine, in free base form, at such a rate as to maintain the reaction temperature of the reaction solution at least 50° C., and the molar ratio of the total amount of epoxide added to the hydroxylamine or mono-substituted hydroxylamine being from about 2:1 to about 2:1.2.

2. The method of claim 1 wherein R' is an alkyl group of 1 to 7 carbon atoms, a haloalkyl group of 1 to 3 carbon atoms and one or two chloro substituents, a hydroxyalkyl group of 1 to 3 carbon atoms, a cyclohexyl group or a phenyl group, $R_1$ and $R_2$ are independently an alkyl group of 1 to 2 carbon atoms or a hydroxyalkyl of 1 to 2 carbon atoms, and Y is an alkylene group of at least 4 carbon atoms and having an even number of carbon atoms in the chain.

3. The method of claim 1 wherein said hydroxylamine or mono-substituted hydroxylamine is hydroxylamine, N-methylhydroxylamine, N-isopropylhydroxylamine or N-ethylhydroxylamine.

4. The method of claim 1 wherein said epoxide is glycidol, ethylene oxide, propylene oxide, 2-methyl-2,3-epoxy-1-propanol, 4-phenyl-2,3-epoxy-1-butanol, 1,4-butanediol diglycidyl ether, epichlorhydrin or 1,2,7,8-diepoxyoctane.

5. The method of claim 1 wherein the reaction temperature of the reaction solution is maintained at from about 50 to about 90° C.

6. The method of claim 1 wherein the reaction temperature of the reaction solution is maintained at from about 70 to about 90° C.

7. The method of claim 1 wherein the epoxide is added to said aqueous solution of hydroxylamine or mono-substituted hydroxylamine at a rate of from about 0.1 to about 4 mol %/min.

8. The method of claim 1 wherein said antioxidant of Structure I is N,N-bis(2,3-dihydroxypropyl)hydroxylamine, N,N-bis(2-methyl-2,3-dihydroxypropyl)hydroxylamine or N,N-bis(1-hydroxymethyl-2-hydroxy-3-phenylpropyl) hydroxylamine.

9. The method of claim 8 wherein said antioxidant of Structure I is N,N-bis(2,3-dihydroxypropyl)hydroxylamine.

* * * * *